United States Patent [19]

Ritter

[11] 4,073,882
[45] Feb. 14, 1978

[54] 5-METHYL-3-M-BUTYL-OCTAHYDROIN-DOLIZINE AS AN ATTRACTANT FOR ANTS

[75] Inventor: Fridolin J. Ritter, Waddinxveen, Netherlands

[73] Assignee: Nederlandse Organisatie voor Toegepast Natuurwetenschappelijk Onderzoek Ten Behoeve Van Nijverheid Handel en Verkeer, The Hague, Netherlands

[21] Appl. No.: 646,611

[22] Filed: Jan. 5, 1976

Related U.S. Application Data

[63] Continuation of Ser. No. 459,358, April 9, 1974, abandoned.

[30] Foreign Application Priority Data

Apr. 19, 1973   United Kingdom ............... 18990/73

[51] Int. Cl.² ................... A01N 17/14; C07D 211/06

[52] U.S. Cl. ................... 424/84; 260/293.53; 424/267

[58] Field of Search ............... 424/84; 260/293.53

[56] References Cited

U.S. PATENT DOCUMENTS 3,294,539   12/1966   Bailey ................... 260/293.53 X
3,717,644    2/1973   Walter ................... 260/293.53

Primary Examiner—Allen J. Robinson
Attorney, Agent, or Firm—Brumbaugh, Graves, Donohue & Raymond

[57] ABSTRACT

5-Methyl-3-normal butyl-octahydroindolizine is a novel substance which is a powerful attractant for ants, especially the Pharach's ant.

It can be prepared from the novel substance 5-methyl-3-normal butyl-6,8-dicarbethoxy-7-keto-octahydroindolizine.

4 Claims, No Drawings

5-METHYL-3-M-BUTYL-OCTAHYDROINDOLIZINE AS AN ATTRACTANT FOR ANTS

This application is a continuation of application Ser. No. 459,358, filed Apr. 9, 1974, now abandoned.

This invention relates to an attractant and especially to a novel attractant for ants, especially the Pharaoh's ant.

BACKGROUND OF THE INVENTION

The term "attractant" is used in its widest sense and includes trail-following compounds such as the trail pheromones. The invention is especially concerned with preparing and providing an attractant for ants such as the Pharaoh's ant and related species.

The use of substances to lure insects into a situation in which they can be killed or rendered harmless is known. One method of doing this is to lure the insects into a particular location and then cause contact with a pesticide, insect hormone or insect pathogen and the insect to be controlled. In such a case there is no need to disperse the insecticide widely and indiscriminately over large areas, but instead the combination of pesticide and attractant can be placed either as a mixture or as closely spaced quantities, in the neighborhood of those places which have to be protected against the harmful influence of the insects.

A further method is to use the attractant in combination with a trap; the insects ay be killed in this trap or may stick fast to a glue on the walls of the trap. These and other methods for using attractants for controlling insects are known and can be used in accordance with the present invention.

Another important application of attractants is to signal the presence, distribution and spread of the insect. Its presence thus can be detected in good time to take the necessary steps for control and it will not be necessary to use a pesticide outside the period of presence of the insects. Moreover, through use of the attractant a much more definite picture of the extent and intensity of an infestation can be obtained. Thus plans for containment are more feasible and control efforts can be more precisely directed.

Ants, such as the Pharaoh's ant, are in many places a great danger for public health and are often very hard to control. Especially in buildings with central heating, in bakeries and laundries, but also in private houses they form a great problem. The Pharaoh's ant has been shown to be a major carrier of human pathogenic micro-organisms in many hospitals (Susan H. Beatson, The Lancet. Feb. 19, 1972, p. 425: "Pharaoh's ants as pathogen vectors in hospital").

In such places, where the use of toxic substances has to be avoided as much as possible, attractants can be of great importance.

THE INVENTION

A novel powerful attractant for ants such as the Pharaoh's ant (*MONOMORIUM PHARAONIS L*) is 5-methyl-3-normal butyl-octahydroindolizine with the formula I (nomenclature according to IUPAC Nomenclature of Organic Chemistry, Section B, page 56 (1957).

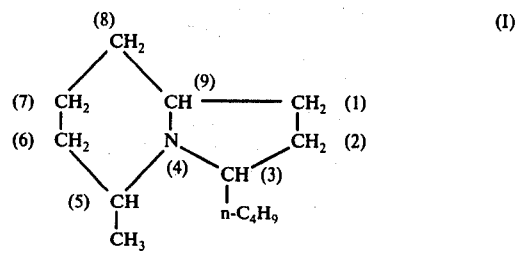

This very active compound I can be obtained by synthesis from the novel compound 5-methyl-3-normal butyl-6,8-dicarbethoxy-7-keto-octahydrindolizine having the formula II.

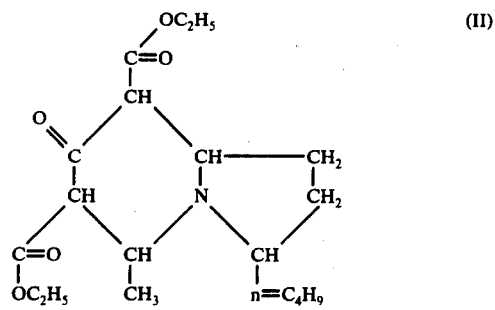

SYNTHETIS (a) A synthetis of 5-methyl-3-n-butyl-6,8-dicarbethoxy-7-keto-octahydroindolizine (II)

A solution of 434 g (2 (Mol) 4-amino-octanal diethylacetal in 2 liters of ethanol (water free) was brought to pH4 with 0.5 N hydrochloric acid. To this solution 404 g (2 Mol) diethyl-3-oxo- glutarate and 88 g (2 Mol) acetaldehyde were added. The reaction mixture was stirred during three days at room temperature and was then brought to pH7 to 8 by addition of sodium carbonate powder.

Gradually a brownish oil of 5-methyl-3-normal butyl-6,8-dicarbethoxy-7keto-octahydrindolizine was formed. This oil was taken up in ether, washed with water and the ether solution was dried with magnesium sulfate. After removal of the ether by distillation 60 g of a brown oil remained (crude II).

A synthesis of 5-methyl-3-n-butyl-octahydroindolizine (I)

A solution was made of 600 g crude (II) in 3 liters of 6 N hydrochloric acid and the boiling solution was refluxed for 2 hours. Subsequently 1500 g amalgamated zinc (prepared from 1400 g Zn and 100 g $HgCl_2$) was added in batches of 100 to 200 g over a period of about one hour. After refluxing the boiling mixture for 20 hours, it was made alkaline with 20 % sodium hydroxide and subsequently it was extracted with ether. After drying with magnesium sulfate and removal of the ether by distillation 210 g of an oil remained. Distillation of this oil under reduced pressure yielded 110 g of a colourlous material (boiling point 58° at 0.25 Hg). This 110 g was dissolved in 2 liters of ethanol and was subsequently hydrogenated by stirring it with hydrogen at atmospheric pressure, using 5 g of Raney nickel as a catalyst, for 15 hours.

After removal of the solvent 110 g was obtained of the product (I): 5-ethyl-3-n-butyl-octahydroindolizine.

Physical properties of 5-methyl-3-n-butyl-octahydroindolizine

According to analysis by combined gas chromatography mass spectometry the product of the synthesis contained the stereoisomers of (I). Each of these will probably be present as the racemic mixture of the optical antipodes.

By distillation over a Micro-Spaltrohr column (plate number 35) it was possible to obtain one of these stereoisomers in pure form. From 110 g crude product 15 g of a pure stereoisomer was obtained with a boiling point at 0.25 mm Hg of 58° C and $n_D^{20} = 1.467$. This stereoisomer showed the following characteristic properties. Kóvats retention index in gaschromatography (See: Anal. Chem. Vol. 36, Nr. 8, p. $31^a$ - July 1964); 1596, 1380 and 1345 respectively on columns with the stationary phases DEGS, OV-17 and OV-101 (i.e. diethyleneglycol succinate and two silicon oils respectively). Mass spectrum: main peaks at m/e 195 (parent peak, corresponding with molecular formula $C_{13}H_{25}N$); 194; 180; 138 (base peak); 136; 124; 95; 82; 70; 69; 68; 67; 55; 44 and 41. Infrared spectrum: bands at about 2950 to 2850; 1450; 1370; 1310; 1295; 1220; 1200; 1190; 1160; 1120; 1100; 1030; and 960 cm$^{-1}$. NMR spectrum: $\sigma$(in ppm) 0.88 (triplet, J = 6.5 Hz), 3 protons; 1.18 (doublet, J = 6.5 Hz), 3 protons; 1.2 to 1.6, 12 protons; 1.6 to 1.9, 4 protons; 2.13, 1 proton; 2.27, 1 proton; 2.52, 1 proton.

These data are in agreement with those to be expected for structure (I).

Biological properties of 5-methyl-3-n-butyl-octahydroindolizine

It has been found tht the compound specified is not only an attractant for ants such as the Pharaoh's ant but that it is also a trail-following agent. When slow acting insecticides, insect hormones or insect pathogens are present at the end of a trail of (I) or at any other spot on this trail, the ants still have an opportunity to return to the place they came from (the nest) and in doing so they may leave a trail of (I) along which other ants go preferentially to the place where the control agent is located. This enhances the value of the compound according to the invention in the control of ants.

Since the effective amounts of (I) are extremely small it is preferred that it should be handled in combination with a fluid or a solid carrier. The substance according to the invention can also be present in a closed spaced, the walls of it being permeable to the vapour of (I). The nature of this carrier is not important. The preparations may contain a poison for ants. It is also possible to bring (I) on or in a sticky surface.

The ants will stick to the surface and can be disposed of. Such means are known in the art.

Under laboratory conditions amounts of $10^{-11}$ to $10^{-5}$ grams per location (a paper strip of 10 × 0.4 cm) gave significant results in choice tests with Pharaoh's ants when compared with controls without the attractant. Very significant results where obtained with amounts of 2.5 × $10^{-7}$ to 3 × $10^{-6}$ grams per location.

When $10^{-10}$ to $10^{-7}$ grams of the compound according to the invention are applied as a thin circle with a circumference length of 47 cm that is in an amount of 0.2 × $10^{-11}$ to 0.2 × $10^{-8}$ grams/cm, workers as well as queens of the Pharaoh's ant followed the trail continuously without departing from it.

The compound was applied as an ethereal solution.

Especially the possibility of attracting queens by this substance is of great importance for the insect's control, as the queens have to be killed to prevent further reproduction. The attraction of the worker ants, however, is also important. When all worker ants are attracted from the nests and are prevented from returning to the nest, the supply of nutrients to the nest is stopped and larvae and remaining queens will die by starvation. Also the workers can be contaminated by control agents as mentioned before, and by returning to the nest they will carry over the contaminating agent; in this way the nest, including the reproductive insects (queens and males), larvae, pupae, and eggs are exterminated. In particular for ants, such as the Pharaoh's ant, where the nests are hard to find, these methods are of great importance for a selective and effective control.

I claim:

1. A process for attracting Pharaoh's ants, *Monomorium Pharaonis L*, which comprises applying the compound 5-methyl-3-n-butyl-octahydroindolizine to a location frequented by the ants in an amount effective to attract the ants.

2. The process according to claim 1 wherein the compound is applied in an amount of $10^{-11}$ grams to $10^{-5}$ grams per location measuring 4 cm$^2$.

3. The process according to claim 2 wherein the compound is applied in an amount of 2.5 × $10^{-7}$ grams to 3 × $10^{-6}$ grams per location measuring 4 cm$^2$.

4. The process according to claim 1 wherein the compound is applied to form a trail in an amount of 0.2 × $10^{-11}$ grams/cm to 0.2 × $10^{-8}$ grams/cm.

* * * * *

UNITED STATES PATENT OFFICE
CERTIFICATE OF CORRECTION

Patent No. 4,073,882  Dated February 14, 1978

Inventor(s) Fridolin J. Ritter

It is certified that error appears in the above-identified patent and that said Letters Patent are hereby corrected as shown below:

First page, in the title, "5-METHYL-3-M-BUTYL-OCTAHYDROINDOLIZINE AS AN ATTRACTANT FOR ANTS" should be --5-METHYL-3-N-BUTYL-OCTAHYDROINDOLIZINE AS AN ATTRACTANT FOR ANTS--;

First page, 4th line of Item 73, after "Nijverheid" insert a comma;

First page, first line of ABSTRACT, "5-Methyl" should be --5-methyl--;

First page, third line of ABSTRACT, "Pharach's" should read --Pharaoh's--;

Column 1, line 1, "3-M" should be --3-N--;

Column 1, line 32, "ay" should read --may--;

Column 2, line 14, "octahydrindolizine" should read --octahydroindolizine--;

Column 2, line 45, "7keto-octahydrindolizine" should read --7-keto-octahydroindolizine--;

Column 2, line 48, "60 g" should read --600 g--;

Column 3, line 7, before "mass" insert --and--;

Column 3, line 15, "$n_D20$" should be --$n_D^{20}$--;

Column 3, line 36, "tht" should read --that--; and

Column 4, line 14, after "47 cm" insert a comma.

Signed and Sealed this

Twenty-second Day of August 1978

[SEAL]

Attest:

RUTH C. MASON
Attesting Officer

DONALD W. BANNER
Commissioner of Patents and Trademarks